United States Patent
Ahnaou et al.

(10) Patent No.: US 8,440,715 B2
(45) Date of Patent: May 14, 2013

(54) TREATMENT OF SLEEP-WAKE DISORDERS

(75) Inventors: Abdallah Ahnaou, Berchem (BE);
Wilhelmus H. L. M. Drinkenburg,
Molenschot (NL); Joseph Palumbo,
Saint Davids, PA (US); Jonathan Sporn,
Princeton, NJ (US)

(73) Assignee: SK Biopharmaceuticals Co., Ltd.,
Seoul (KR)

( * ) Notice: Subject to any disclaimer, the term of this patent is extended or adjusted under 35 U.S.C. 154(b) by 444 days.

(21) Appl. No.: 11/921,995

(22) PCT Filed: Jun. 7, 2006

(86) PCT No.: PCT/US2006/022407
§ 371 (c)(1),
(2), (4) Date: Mar. 10, 2009

(87) PCT Pub. No.: WO2006/133393
PCT Pub. Date: Dec. 14, 2006

(65) Prior Publication Data
US 2009/0312416 A1    Dec. 17, 2009

Related U.S. Application Data

(60) Provisional application No. 60/688,638, filed on Jun. 8, 2005.

(51) Int. Cl.
*A01N 47/10* (2006.01)
*A01N 33/02* (2006.01)
*A01N 33/18* (2006.01)
*A01N 33/24* (2006.01)
*A61K 31/27* (2006.01)
*A61K 31/135* (2006.01)
*A61K 31/04* (2006.01)

(52) U.S. Cl.
USPC ............................ 514/478; 514/646; 514/741

(58) Field of Classification Search .................. None
See application file for complete search history.

(56) References Cited

U.S. PATENT DOCUMENTS

| | | | |
|---|---|---|---|
| 4,335,138 A | 6/1982 | Wieersdorff et al. | |
| 5,705,640 A | 1/1998 | Choi et al. | |
| 5,756,817 A * | 5/1998 | Choi et al. ............ | 560/115 |
| 5,955,499 A | 9/1999 | Choi et al. | |
| 6,140,532 A | 10/2000 | Choi et al. | |
| 6,562,867 B2 | 5/2003 | Plata-Salaman et al. | |
| 6,589,985 B2 | 7/2003 | Plata-Salaman et al. | |
| 7,078,436 B2 | 7/2006 | Plata-Salaman et al. | |
| 2005/0203130 A1 | 9/2005 | Buntinx | |

FOREIGN PATENT DOCUMENTS

| | | |
|---|---|---|
| JP | 9-503231 | 3/1997 |
| WO | WO 96/24577 | 2/1996 |
| WO | WO 96/07637 | 3/1996 |
| WO | WO 2006/133393 | 3/1996 |
| WO | WO 98/15526 | 10/1996 |

OTHER PUBLICATIONS

Lammers et al., "Pharmacological management of narcolepsy", Expert Opin. Pharmacother., 2003, vol. 4 No. 10, pp. 1739-1746.*
International Search Report and Written Opinion dated Nov. 13, 2006.
Narcolepsy: Treatment Issues, Thomas Roth (J Clin Psychiatry 2007;68 [suppl 13]:16-19).
The Search Report by the Taiwan Intellectual Property Office, issued on Dec. 14, 2011, in the corresponding Taiwanese patent application No. 95120134. (Englsih translation only.).
Black JE, et al. "Narcolepsy and syndromes of primary excessive daytime somnolence" seminars in Neurology 2004; 24(3):271-282.
Diagnostic and Statistical Manual of Mental Disorders, Fourth Edition, Published by the American Psychiatric Association Washington, DC, 1994.
Goodman & Gilman's The Pharmacological Basis of Therapeutics, Tenth Edition, 2001.
NovaScreen, dated: Oct. 24, 1994.

* cited by examiner

*Primary Examiner* — Jeffrey S. Lundgren
*Assistant Examiner* — Stephanie Springer
(74) *Attorney, Agent, or Firm* — Myers Bigel Sibley & Sajovec, P.A.

(57) ABSTRACT

This invention is directed to a method of treating Excessive daytime Sleepiness (EDS) in a subject, comprising the step of administering a therapeutically effective amount of a compound of Formula (I): Formula (I) or a pharmaceutically acceptable salt or ester thereof wherein Rx is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms; x is an integer of 1 to 3, with the proviso that R may be the same or different when x is 2 or 3; $R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms; $R_1$ and $R_2$ can be joined to form a 5 to 7-membered heterocycle substituted with a member selected from the group consisting of hydrogen, alkyl, and aryl groups, wherein the cyclic compound can comprise 1 to 2 nitrogen atoms and 0 to 1 oxygen atom, wherein the nitrogen atoms are not directly connected with each other or with the ox en atom.

(I)

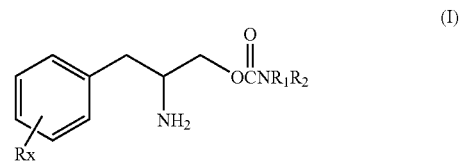

15 Claims, No Drawings

TREATMENT OF SLEEP-WAKE DISORDERS

RELATED APPLICATIONS

This application is a 35 U.S.C. §371 national phase application of PCT International Application No. PCT/LJS2006/022407, filed Jun. 7, 2006, which claims priority to U.S. Provisional Application No. 60/688,638 filed Jun. 8, 2005.

BACKGROUND OF THE INVENTION

1. Field of the Invention

The present invention relates generally to the fields of pharmacology, neurology and psychiatry and to methods of treating sleep-wake disorders. More specifically, this invention provides methods for the use of certain carbamate compounds for the treatment of sleep-wake disorders including excessive daytime sleepiness and pathological somnolence.

2. Description of Related Art

Excessive Daytime sleepiness (EDS) or pathological somnolence refers to excessive sleepiness during the day associated with a wide variety of disorders of sleep and wakefulness. These disorders may be primary sleep disorders such as narcolepsy or they may be the result of some other medical condition that has an adverse effect on sleep patterns.

Excessive Daytime Sleepiness (EDS), is the primary complaint of patients seen in sleep clinics, affects up to 12% of the general population. The effects of EDS can be debilitating and even life threatening. Patients with EDS may exhibit psychosocial distress, decreased work or school performance, and increased risk for accidents. The differential diagnosis of EDS requires objective assessments, such as polysomnography and the Multiple Sleep Latency Test.

There are four major causes of EDS: (1) central nervous system (CNS) pathologic abnormalities, such as narcolepsy and idiopathic CNS hypersomnia; (2) qualitative or quantitative sleep deficiencies, such as sleep apnea, obstructive sleep apnea and insufficient nocturnal sleep, due to e.g. chronic and acute pain resulting from various medical conditions including Parkinson's disease, urinary incontinence, multiple sclerosis fatigue, ADHD, Alzheimer's disorder, Major Depression, Bipolar Disorder and cardiac ischemia; (3) misalignments of the body's circadian pacemaker with the environment (e.g. jet lag or shift work); and (4) drugs, which can increase sleepiness either therapeutically or as a side effect.

Depending on etiology, management strategies for EDS include extension of time in bed, naps, surgery, various medical devices (e.g., oral appliances, continuous positive airway pressure), and pharmacotherapy.

Fatigue and excessive sleepiness are also common symptoms of a major depressive disorder and other mood disorders such as Bipolar Disorder, and can be adverse side effects associated with antidepressant drug therapy or may be residual symptoms inadequately treated with antidepressant therapy. In addition, patients sometimes suffer sleep related side effects associated withdrawal of antidepressant therapy.

Narcolepsy is a common cause of EDS and is a disabling neurological disorder that was first recognized 118 years ago by Gélineau, J. B. (De la narcolepsy, Gazette des Hopitaux Paris (1880) 53: 626-628). Narcolepsy is a chronic disorder characterized by intermittent sleep attacks, persistent, excessive daytime sleepiness and abnormal rapid eye movement ("REM") sleep manifestations, such as sleep-onset REM periods, cataplexy, sleep paralysis and hypnagogic hallucinations, or both. Most patients with narcolepsy also have disrupted nocturnal sleep.

For a review of narcolepsy, see generally Chokroverty, S. (ed.), Sleep Disorders Medicine Basic Science, Technical Considerations, and Clinical Aspects, 22nd edition, Butterworth Heinemann, Boston, Mass. U.S.A. 1999; Aldrich, M., Sleep Medicine, Oxford University Press, New York, N.Y. U.S.A. 1999; Vgnotzas, A. N. et al., Annu. Rev. Med. (1999) 50:387-400; and Guillenminault, C., Narcolepsy Syndrome in Principles and Practice of Sleep Medicine, $2^{nd}$ edition (Kryger, M. H., et al. (eds.), (W. B. Saunders Philadelphia, Pa. U.S.A. 1989), pages 338-246).

The symptoms of narcolepsy include excessive daytime sleepiness (EDS), hypnagogic and hypnopompic hallucinations (hallucinations during transitions into and out of sleep, respectively), cataplexy (sudden and reversible loss of muscle tone), sleep paralysis (an inability to move at sleep onset or awakening) and REM sleep at sleep onset (Guilleminault, C. 1989). In narcoleptics, sleep occurs at inappropriate times and in dangerous and embarrassing situations. Although total sleep time is near normal, nighttime sleep is disrupted by frequent awakenings (Mitler, M. et al., Psych Clin. N. Amer. (1987) 10:593-606).

Cataplexy, a temporary, partial or complete paralysis due to a sudden loss of muscle tone, with unimpaired consciousness, is typically triggered by sudden strong emotions, such as those accompanying laughter, anger and embarrassment. In some patients, status cataplecticus, or periods of repetitive loss of muscle tone, occurs and can last for hours or days.

Narcolepsy has also been reported to occur in other animals and has been most intensively studied in canines (Foutz, A. S., et al., (1979) Sleep 1:413-421; Nishino, S, and Mignot, E. (1997) Prog. Neurobiol. 52:27-78; Cederberg, R., et al., (1998) Vet. Rec. 142, 31-36). Canine narcolepsy in Doberman pinschers and Labrador Retrievers is transmitted as an apparently single gene autosomal recessive trait with full penetrance, canarc-1 (Foutz, A. S., et al., (1979) Sleep 1:413-421; Baker, T. L. and Dement, W. C. (1985), Canine narcolepsy—cataplexy syndrome: evidence for an inherited monoaminergic-cholinergic imbalance in Brain Mechanisms of Sleep, D. J. McGinty, R. Drucker-Colin, A. Morrison, and P. L. Parmeggiani, eds. (N.Y.: Raven Press), pages 199-233).

A large number of physiological and pharmacological studies have demonstrated a close similarity between human and canine narcolepsy (Baker, T. L. and Dement, W. C. (1985) and Nishino, S, and Mignot, E. (1997)). These animals have all the major symptoms defining narcolepsy in humans, including episodes of cataplexy.

Canine narcoleptics also exhibit excessive daytime sleepiness and interrupted sleep periods (Kaitin, K. I. et al., Electroenceph. Clin. Neurophysiol. (1986) 64:447-454). Cholinergic antagonists block cataplexy in both canine and human narcoleptics (Delashaw et al., (1979) Exp. Neurology 66:745-757). α1 blockers (such as prazosin) exacerbate cataplexy in dogs and humans and can produce status cataplecticus in both species (Mignot et al., (1988) Brain Res. 444:184-188; Guilleminault et al., (1988) The Lancet 2: 511).

Drugs used to treat cataplexy and excessive sleepiness in humans are also effective in narcoleptics dogs (Baker and Dement, 1985). Narcolepsy usually does not develop until adolescence in humans, but it can be seen as early as three or as late as 45 years of age or older (Yoss and Daly, (1960) Pediatrics 25:1025-1033; Billiard, (1985) Ann. Clin. Res 17:220-226). The appearance of cataplexy, as a proxy variable for the onset of narcolepsy/cataplexy, in canine narcolepsy, develops between 4 and 24 weeks of age.

Approximately 250,000 Americans have narcolepsy (Aldrich, M. S., New Eng. J. Med. (1990) 323:389-394). Although familial cases of narcolepsy have been reported, most human occurrences are sporadic, and the disorder is generally believed to be multigenic and environmentally influenced (Honda, Y., and Matsuki, K., Genetic Aspects of Narcolepsy in Handbook of Sleep Disorders, M. Thorpy (ed.) (Marcel Dekker, Inc., New York, N.Y. 1990), pages 217-234). One predisposing genetic factor is a specific HLA-DQ allele, HLA-DQB1*0602 (Matsuki, K., et al., (1992) Lancet 339: 1052. Mignot, E., et al., (1994) Sleep 17:S60-S67; Mignot, E. (1998) Neurology 50:S16-S22). Approximately 95% of narcoleptics have this HLA haplotype, compared to only 30% of the general population (Aldrich, M. S., New Eng. J Med. (1990) 323:389-394).

An autoimmune mechanism has been reported in some HLA-associated diseases such as juvenile diabetes, celiac disease, systemic lupus erythematosus and rheumatoid arthritis (Sinha, A. et al., Science (1990) 248:1380-1388); however, all attempts to date to test the autoimmune hypothesis for narcolepsy have failed (Mignot, E., et al., Adv. Neuroimmunol. (1995) 5:23-37).

It has recently been reported that narcolepsy is linked to dysfunction of the newly discovered hypocretin (Hcrt) (orexin) peptide system. This report was based on a deletion in the transcripts of the hypocretin receptor 2 (Hcrtr2) gene in narcoleptic Dobermans and Labradors (Lin, L. et. al., Cell (1999) 97:365-376). Chemelli et al. created Hcrt knockout mice that have abnormalities of sleep control resembling aspects of narcolepsy (Chemelli, R. M. et al., Cell (1999) 98:437-451), as well.

Narcolepsy requires long-term management of symptoms (Fry, J., Neurology (1998) 50(2 Suppl 1):S8-15). Interventions can be nonpharmacologic, such as lifestyle changes, and pharmacologic, for relief of daytime sleepiness, cataplexy, sleep paralysis, hypnagogic hallucinations, and/or hypnopompic hallucinations.

Pharmacologic treatment of narcolepsy has depended on the use of central nervous system (CNS) stimulants to increase wakefulness or to reduce the number and severity of cataplectic attacks or hypnagogic hallucinations. CNS stimulants can be effective in relieving the sleepiness of narcolepsy; however, extremely high doses are necessary to restore alertness to normal levels (Mitler, M. et al., Sleep (1993) 16:306-317). Such doses can have very dangerous side effects.

Because of these side effects, most narcoleptics use stimulants only when absolutely needed or continuously use low-level doses not capable of restoring normal levels of alertness. Periodic "drug holidays" can sometimes be employed to maintain the effectiveness of stimulants (Mitler, M. S. Sleep (1994) 17:S103-S106). Frequent naps can be effective in permitting periods of waking alertness (Aldrich, M. S., Neurology (1992) 42(S6):34-43). Cataplexy can sometimes be treated successfully with tricyclic antidepressants or selective serotonin reuptake inhibitors (SSRI's), among other medications. Both tricyclic antidepressant drugs and SSRI's all appear to act by producing metabolites that activate noradrenergic receptors (Nishino, S. et al., Sleep (1993) 16:706-712; Mignot, E. et al., Psychopharmacology (1993) 113:76-82). Even with these treatments, accidents due to sleepiness and cataplexy are common and professional and educational attainments are significantly reduced in narcoleptics (Broughton, W. A. and Broughton, R. J., Sleep (1994) 17:S45-S49).

Excessive daytime sleepiness (EDS) or pathological somnolence, whether due to narcolepsy or other causes, is disabling and potentially dangerous since it produces episodes of unintended sleep, reduced attention, and performance errors. EDS, regardless of cause, is linked to a variety of transportation and industrial accidents and cause decreased job performance and considerable subjective distress. A therapeutic agent that reduces or eliminates EDS would have important implications not only for individual patients, but also for public health and safety.

SUMMARY OF THE INVENTION

The present invention is directed to a method of treating sleep disorders in a subject, including excessive daytime sleepiness (EDS) or pathological somnolence comprising, administering to a subject in need of such treatment, a therapeutically effective amount of a compound of the Formula (I):

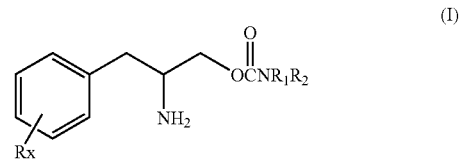

(I)

or a pharmaceutically acceptable salt or ester thereof wherein
Rx is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms;
x is an integer of 1 to 3, with the proviso that R may be the same or different when x is 2 or 3;
$R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms; $R_1$ and $R_2$ can be joined to form a 5 to 7-membered heterocycle substituted with a member selected from the group consisting of hydrogen, alkyl, and aryl groups, wherein the cyclic compound can comprise 1 to 2 nitrogen atoms and 0 to 1 oxygen atom, wherein the nitrogen atoms are not directly connected with each other or with the oxygen atom.

Embodiments of the invention include a method of treating Excessive Daytime Sleepiness (EDS) in a subject, comprising the step of administering, to a subject in need of such treatment, a therapeutically effective amount an enantiomer of Formula I substantially free of other enantiomers or an enantiomeric mixture wherein one enantiomer of Formula I predominates;

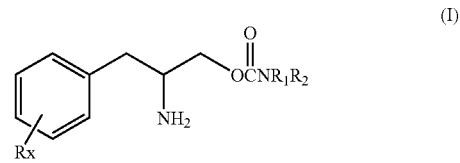

(I)

or a pharmaceutically acceptable salt or ester thereof wherein
Rx is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms;
x is an integer of 1 to 3, with the proviso that R may be the same or different when x is 2 or 3;
$R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms; $R_1$ and $R_2$ can be joined to form a 5 to 7-membered heterocycle substituted with a member selected from the group consisting of hydrogen, alkyl, and aryl groups, wherein the cyclic compound can comprise 1 to 2 nitrogen atoms and 0 to 1 oxygen atom, wherein the nitrogen atoms are not directly connected with each other or with the oxygen atom. Preferably, wherein Rx, R1 and R2 are all selected from hydrogen. Preferably wherein one enantiomer selected from the group consisting of Formula I predominates to the extent of about 90% or greater.

More preferably, wherein one enantiomer selected from the group consisting of Formula I predominates to the extent of about 98% or greater.

Embodiments of the invention include the use, for the preparation of a medicament for the treatment of EDS, of an enantiomer selected from the group consisting of Formula I

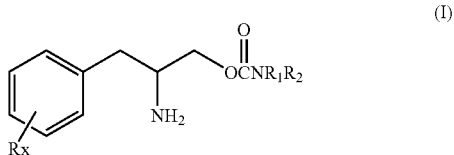

(I)

or a pharmaceutically acceptable salt or ester thereof wherein Rx is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms;

x is an integer of 1 to 3, with the proviso that R may be the same or different when x is 2 or 3;

$R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms; $R_1$ and $R_2$ can be joined to form a 5 to 7-membered heterocycle substituted with a member selected from the group consisting of hydrogen, alkyl, and aryl groups, wherein the cyclic compound can comprise 1 to 2 nitrogen atoms and 0 to 1 oxygen atom, wherein the nitrogen atoms are not directly connected with each other or with the oxygen atom.

Embodiments of the invention include a method include the use of an enantiomer of Formula I substantially free of other enantiomers that is the enantiomer of Formula I b (R)-(beta-amino-benzenepropyl) carbamate or (O-carbamoyl-(D)-phenylalaninol) or an enantiomeric mixture wherein the enantiomer of Formula Ib (R)-(beta-amino-benzenepropyl) carbamate or (O-carbamoyl-(D)-phenylalaninol) predominates.

Formula Ib

Formula Ib (R)-(beta-amino-benzenepropyl) carbamate or (O-carbamoyl-(D)-phenylalaninol) wherein the enantiomer of Formula Ib (R)-(beta-amino-benzenepropyl) carbamate or (O-carbamoyl-(D)-phenylalaninol) predominates to the extent of about 90% or greater. More preferably, an enantiomer of Formula Ib (R)-(beta-amino-benzenepropyl) carbamate or (O-carbamoyl-(D)-phenylalaninol) predominates to the extent of about 98% or greater.

Embodiments of the invention include a methods wherein the cause of the EDS is chosen from the group consisting of; central nervous system (CNS) pathologic abnormalities, stroke, narcolepsy, idiopathic CNS hypersomnia; sleep deficiency, sleep apnea, obstructive sleep apnea, insufficient nocturnal sleep, chronic pain, acute pain, Parkinson's disease, urinary incontinence, multiple sclerosis fatigue, Attention Deficit Hyperactivity Disorder (ADHD), Alzheimer's disorder, Major Depression, Bipolar Disorder, cardiac ischemia; misalignments of the body's circadian pacemaker with the environment, jet lag, shift work); and sedating drugs.

DETAILED DESCRIPTION OF THE INVENTION

The present invention is based in part on the discovery that phenylalkylamino carbamates of Formula I have novel and unique pharmacological properties. These compounds have been shown in both animal models and in studies in humans to have an activating or energizing effect. Although the precise mechanism of action is not completely understood, it is believed that these compounds do not work by the same mechanisms as most other known stimulant drugs in producing their activating or energizing like effects. However, in animals, treatment with a phenylalkylamino carbamate of Formula 1 at 30 mg/kg strongly increased active wakefulness at the expense of time spent in light sleep, deep sleep and REM sleep during the first 3 to 4 hours after the administration. A rebound effect was seen between 4-10 hours following administration of the compound, as an increase in time spent in deep sleep that gradually decreased in the hours thereafter. Moreover, the compound of Formula 1 affected other sleep-wake parameters; more specifically it increased significantly the number of shifts from light sleep and REM sleep into wakefulness as well as lengthened the latency of REM sleep onset.

For these two reasons the compounds of Formula 1 are especially suitable for use as treatment for EDS and other disorders where it is desirable to increase the amount of time a subject spends awake. Thus, these compounds can be safely used for this purpose to provide effective treatment of EDS regardless of the precise etiology of the underlying sleep disturbance.

Typically, doses of a compound of Formula I would start at 10-25 mg/day and increase in increments of about 10-25 mg./day per week until side effects intervene or an adequate response is obtained, with a maximum dose in the range of 500 mg/day to 2000 mg/day.

One compound of Formula I consists of the (D) enantiomer of the structure shown below wherein Rx=R1=R2=hydrogen, in the structure shown below the amine group is directed down from the plane of the paper, This compound is the (R) enantiomer, if named by structure and is therefore (R)-(beta-amino-benzenepropyl) carbamate. This compound is the dextrorotary enantiomer and can therefore also be named O-carbamoyl-(D)-phenylalaninol and is referred to herein as the "test compound". The two chemical names may be used interchangeably in this specification.

This compound has been tested in numerous animal models and in humans and has demonstrated effects including strongly increased active wakefulness at the expense of time spent in light sleep, deep sleep and REM sleep during the first 3 to 4 hours after the administration. In addition, this compound increased significantly the number of shifts from light sleep and REM sleep into wakefulness as well as lengthened the latency of REM sleep onset. The compound also shows stimulant or energizing effects in the Spontaneous Locomotor Activity in Mice and Rats model.

Thus in some embodiments, the present invention is directed to a method of preventing or reducing the severity of EDS. The method comprising administering to a subject in need thereof a therapeutically effective amount of a compound selected from the group consisting of phenylalkylamino carbamates of the following Formula I:

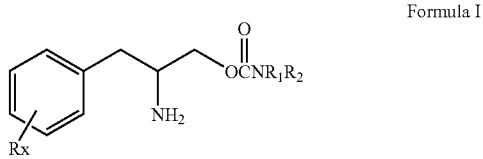

Formula I or an enantiomer, diastereomer, racemate or mixtures thereof, or a pharmaceutically acceptable salt or ester thereof wherein;

Rx is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms; x is an integer of 1 to 3, with the proviso that R may be the same or different when x is 2 or 3;

$R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms; $R_1$ and $R_2$ can be joined to form a 5 to 7-membered heterocycle substituted with a member selected from the group consisting of hydrogen, alkyl, and aryl groups, wherein the cyclic compound can comprise 0 to 2 nitrogen atoms and 0 to 1 oxygen atoms, wherein the nitrogen atoms are not directly connected with each other or with the oxygen atom and the pharmaceutically acceptable salts and esters thereof.

The present method also includes the use of a compound selected from the group consisting Formula I wherein Rx, R1 and R2 are preferably selected from hydrogen, this is Formula Ia below;

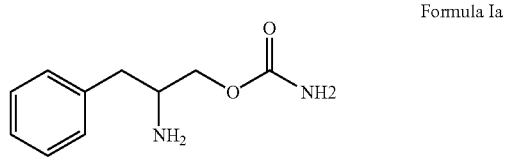 [SMILES: NC(=O)OCC(N)Cc1ccccc1]

Formula Ia

The present method also includes the use of the D enantiomer selected from the group consisting of Formula I or an enantiomeric mixture wherein the D enantiomer selected from the group consisting of Formula Ia predominates wherein Rx, R1 and R2 are preferably selected from hydrogen, this is O-carbamoyl-(D)-phenylalaninol. Formula Ib below; (note-in Formula Ib, i.e. the D enantiomer, as shown, the amine group on the chiral carbon is orientated into the plane of the paper)

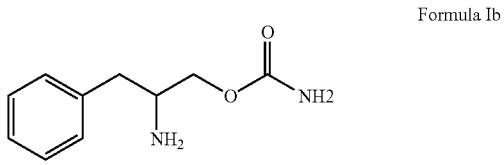 [SMILES: NC(=O)OCC(N)Cc1ccccc1]

Formula Ib

For enantiomeric mixtures wherein one enantiomer selected from the group consisting of Formula I predominates, preferably, an enantiomer selected from the group consisting of Formula I predominates to the extent of about 90% or greater. More preferably, an enantiomer selected from the group consisting of Formula I predominates to the extent of about 98% or greater.

The compounds of Formula I can be synthesized by methods known to a skilled artisan. The salts and esters of the compounds of Formula (I) can be produced by treating the compound with a suitable mineral or organic acid (HX) in suitable solvent or by other means well known to those of skill in the art.

Details of the above reactions schemes for synthesizing compounds of Formula (I) as well as representative examples on the preparation of specific compounds have been described in U.S. Pat. Nos. 5,705,640, 5,955,499, 6,140,532, all incorporated herein by reference in their entirety.

From Formula I it is evident that some of the compounds of the invention have at least one and possibly more asymmetric carbon atoms. It is intended that the present invention include within its scope the stereochemically pure isomeric forms of the compounds as well as their racemates. Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereoselective reactions.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, Third Edition, John Wiley & Sons, 1999. The protecting groups may be removed at a convenient subsequent stage using methods known from the art.

Other embodiments of the invention include the use, for the preparation of a medicament for the treatment of EDS, of one of the compounds or enantiomers or enantiomeric mixtures described above or a pharmaceutically acceptable salt or ester thereof.

All of the U.S. patents that have been mentioned above in connection with compounds used in the present invention are incorporated herein by reference.

Definitions

For convenience, certain terms employed in the specification, examples, and appended claims are collected here. It is to be understood that this invention is not limited to the particular methodology, protocols, animal species or genera, and reagents described, as such may vary. It is also to be understood that the terminology used herein is for the purpose of describing particular embodiments only, and is not intended to limit the scope of the present invention that will be limited only by the appended claims.

As used herein the term "Excessive Daytime Sleepiness" (EDS) shall be used interchangeably with the term "pathological somnolence" and shall mean a condition in which an individual feels very drowsy during the day and has an difficult to resist urge to fall asleep, whether or not the individual has gotten enough nighttime sleep. Excessive sleepiness is defined as sleepiness occurring in a situation when an individual would be expected to be awake and alert. Clinically the symptoms of EDS can be quantified and measured in a variety of ways, including but not limited to; the Multiple Sleep Latency Test (MSLT) (See Carskadon M A and Dement W C, *Sleep* 1982;5 Suppl 2:S67-72), the Maintenance of Wakefulness Test (MWT) (See, Mitler M M, et al. *Electroencephalogr Clin Neurophysiol*, 1982; 53(6):658-61) or the Stanford Sleepiness Scale (SSS) (See, Hoddes E et al., *Psychophysiology*, 1973; 10(4):431-6) (See also, Arand D et al. *Sleep*, 2005; 28(1):123-144). The causes of EDS are multiple and the use of the term EDS herein is not intended to imply any particular cause or etiology. People with EDS frequently doze, nap, or fall asleep in situations where they need or want to be fully awake and alert. The diagnosis can be made when the symptoms of EDS interfere significantly with a person's ability to concentrate and perform daily tasks and routines such as work, family responsibilities, driving a car or operating other hazardous machinery or general quality of life.

As used herein, the term "mental disorder" and "mental illness" refer to those provided in the Diagnostic and Statistical Manual (DSM IV), American Psychological Association (APA). These mental disorders include, but are not limited to affective disorders, Major Depression and related depressive disorders. Examples of affective disorders include mood disorders, manic disorder, major depressive disorder and bipolar affective disorder. Mood disorders include, but are not limited to, depressive disorders including Major Depression with or without psychotic features, dysthymic disorder, bipolar disorders (I and II) and cyclothymic disorders.

As used herein the term "subject", refers to an animal, preferably a mammal, and most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of one or more of the signs or symptoms of the disease or disorder being treated.

The term "prophylactically effective amount" is intended to mean that amount of a pharmaceutical drug that will prevent or reduce the risk of occurrence of the biological or medical event that is sought to be prevented, in a tissue, a system, animal or human, by a researcher, veterinarian, medical doctor or other clinician.

The term "pharmaceutically acceptable salts or esters" shall mean non-toxic salts or esters of the compounds employed in this invention which are generally prepared by reacting the free acid with a suitable organic or inorganic base or the free base with a suitable organic or inorganic acid. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, potassium, salicylate, sodium, stearate, subacetate, succinate, tannate, tartrate, teoclate, tosylate, triethiodide, valerate.

The terms "subject" or "patient" are used herein interchangeably and as used herein mean any mammal, including but not limited to human beings including a human patient or subject, to which the compositions of the invention can be administered. The term mammals include human patients and non-human primates, as well as experimental animals such as rabbits, rats, and mice, and other animals.

The term "a patient in need of treatment" as used herein will refer to any subject or patient who currently has or may develop any of the above syndromes or disorders, including any condition or disorder in which the subject spends an excessive amount of time in a sleep state or unable to maintain a satisfactory degree of wakefulness during a period of the day when wakefulness is required or desired, or any other disorder in which the patient's present clinical condition or prognosis could benefit from the administration of one or more compounds of Formula (I) alone or in combination with another therapeutic intervention including but not limited to another medication.

The term "treating" or "treatment" as used herein, refers to any indicia of success in the prevention or amelioration of an injury, pathology or condition, including any objective or subjective parameter such as abatement; remission; diminishing of symptoms or making the injury, pathology, or condition more tolerable to the patient; slowing in the rate of degeneration or decline or worsening of the illness; making the final point of worsening less debilitating; or improving a subject's physical or mental well-being. The treatment or amelioration of symptoms can be based on objective or subjective parameters; including the results of a physical examination, sleep study, neurological examination, and/or psychiatric evaluations. Accordingly, the term "treating" or "treatment" includes the administration of the compounds or agents of the present invention to provide increased alertness or decreased need for or desire for sleep. In some instances, treatment with the compounds of the present invention will be done in combination with other compounds to provide increased alertness or decreased need for or desire for sleep or to prevent, inhibit, or arrest the progression of EDS.

The term "therapeutic effect" as used herein, refers to the effective provision of the above-described action.

The term "a therapeutically effective amount" as used herein means a sufficient amount of one or more of the compounds of the invention to produce a therapeutic effect, as defined above, in a subject or patient in need of such neuroprotection treatment.

As used herein the term "concomitant administration" or "combination administration" of a compound, therapeutic agent or known drug with a compound of the present invention means administration of a known medication or drug and, in addition, the one or more compounds of the invention at such time that both the known drug and the compound will have a therapeutic effect. In some cases this therapeutic effect will be synergistic. Such concomitant administration can involve concurrent (i.e. at the same time), prior, or subsequent administration of the known drug with respect to the administration of a compound of the present invention. A person of ordinary skill in the art, would have no difficulty determining the appropriate timing, sequence and dosages of administration for particular drugs and compounds of the present invention.

In addition, in some embodiments, the compounds of this invention will be used, either alone or in combination with each other or in combination with one or more other therapeutic medications as described above, or their salts or esters, for manufacturing a medicament for the purpose of providing treatment for EDS or related conditions to a patient or subject in need thereof.

As used herein the term "$C_1$-$C_4$ alkyl" refers to substituted or unsubstituted aliphatic hydrocarbons having from 1 to 4 carbon atoms. Specifically included within the definition of "alkyl" are those aliphatic hydrocarbons that are optionally substituted. In a preferred embodiment of the present invention, the $C_1$-$C_4$ alkyl is either unsubstituted or substituted with phenyl.

As used herein the term "test compound" (tc) or "TEST COMPOUND" (TC) means the hydrochloride salt of (R)-(beta-amino-benzenepropyl) carbamate which can also be named O-carbamoyl-(D)-phenylalaninol. This compound is the (R) enantiomer, shown as Formula Ib, structurally and is also the dextro-rotary enantiomer. Test compound is also referred to as R228060 in the legend to Tables 1-4.

The term "phenyl", as used herein, whether used alone or as part of another group, is defined as a substituted or unsubstituted aromatic hydrocarbon ring group having 6 carbon atoms. Specifically included within the definition of "phenyl" are those phenyl groups that are optionally substituted. For example, in a preferred embodiment of the present invention, the, "phenyl" group is either unsubstituted or substituted with halogen, $C_1$-$C_4$ alkyl, $C_1$-$C_4$ alkoxy, amino, nitro, or cyano.

Methods are known in the art for determining therapeutically and prophylactically effective doses for the instant pharmaceutical composition. For example, for use as a treatment for EDS, the compounds of this invention can be employed at a daily dose in the range of about 0.1 mg to 1000 mg usually on a regimen of 1 to 3 times per day, for an average adult human. The effective amount, however, may be varied depending upon the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The compound may be administered to a subject by any conventional route of administration, including, but not limited to, intravenous, oral, subcutaneous, intramuscular, intradermal and parenteral. Depending on the route of administration, compounds of Formula (I) can be constituted into any form. For example, forms suitable for oral administration include solid forms, such as pills, gelcaps, tablets, caplets, capsules (each including immediate release, timed release and sustained release formulations), granules, and powders. Forms suitable for oral administration also include liquid forms, such as solutions, syrups, elixirs, emulsions, and suspensions. In addition, forms useful for parenteral administration include sterile solutions, emulsions and suspensions.

To prepare the pharmaceutical compositions of this invention, one or more compounds of formula (I) or salt thereof as the active ingredient is intimately admixed with a pharmaceutical carrier according to conventional pharmaceutical compounding techniques. Carriers are necessary and inert pharmaceutical excipients, including, but not limited to, binders, suspending agents, lubricants, flavorings, sweeteners, preservatives, dyes, and coatings. In preparing compositions in oral dosage form, any of the usual pharmaceutical carriers may be employed. For example, for liquid oral preparations, suitable carriers and additives include water, glycols, oils, alcohols, flavoring agents, preservatives, coloring agents and the like; for solid oral preparations, suitable carriers and additives include starches, sugars, diluents, granulating agents, lubricants, binders, disintegrating agents and the like.

For parenteral use, the carrier will usually comprise sterile water or saline solution, though other ingredients, for example, for purposes such as aiding solubility or for preservation, may be included. Injectable suspensions may also be prepared, in which case appropriate liquid carriers, suspending agents and the like may be employed.

Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. The tablets or pills can be coated or otherwise compounded to provide a dosage form affording the advantage of prolonged action. For example, the tablet or pills can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

Active drug may also be delivered by the use of monoclonal antibodies as individual carriers to which the compound molecules are coupled. Active drug may also be coupled with soluble polymers as targetable drug carriers. Such polymers can include polyvinyl-pyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

Preferably these compositions are in unit dosage forms such as tablets, pills, capsules, powders, granules, sterile parenteral solutions or suspensions, metered aerosol or liquid sprays, drops, ampoules, auto-injector devices or suppositories, for oral parenteral, intranasal, sublingual or rectal administration, or for administration by inhalation or insufflation.

Alternatively, the composition may be presented in a form suitable for once-weekly or once-monthly administration; for example, an insoluble salt of the active compound, such as the decanoate salt, may be adapted to provide a depot preparation for intramuscular injection.

The pharmaceutical compositions herein will contain, per dosage unit, e.g., tablet, capsule, powder, injection, teaspoonful, suppository and the like, an amount of the active ingredient necessary to deliver an effective dose as described above. For example, the pharmaceutical compositions herein can contain, per unit dosage unit, from about 10 to about 1000 mg of the active ingredient. Preferably, the range is from about 25 to about 200 mg of the active ingredient.

In some embodiments of the present invention carbamate compounds suitable for use in the practice of this invention will be administered either singly or concomitantly with at least one or more other compounds or therapeutic agents, e.g., with other agents that tend to increase arousal or alertness. In these embodiments, the present invention provides methods to treat or prevent EDS in a patient. The method includes the step of; administering to a patient in need of treatment, an effective amount of one of the carbamate compounds disclosed herein in combination with an effective amount of one or more other compounds or therapeutic agents that have the ability to provide advantageous combined effects such as the ability to augment the activating effects of the compounds of the invention.

It is understood that substituents and substitution patterns on the compounds of the present invention can be selected by one of ordinary skill in the art to provide compounds that are chemically stable and that can be readily synthesized by techniques known in the art as well as the methods provided herein.

The present invention includes the use of isolated enantiomers of Formula I. In one preferred embodiment, a pharmaceutical composition comprising the isolated S-enantiomer of Formula I is used to provide treatment to a subject. In another preferred embodiment, a pharmaceutical composition comprising the isolated R-enantiomer of Formula I is used to provide treatment to a subject.

The present invention also includes the use of mixtures of enantiomers of Formula I. In one aspect of the present invention, one enantiomer will predominate. An enantiomer that predominates in the mixture is one that is present in the mixture in an amount greater than any of the other enantiomers present in the mixture, e.g., in an amount greater than 50%. In one aspect, one enantiomer will predominate to the extent of 90% or to the extent of 91%, 92%, 93%, 94%, 95%, 96%, 97% or 98% or greater. In one preferred embodiment, the enantiomer that predominates in a composition comprising a compound of Formula I is the S-enantiomer of Formula I.

The present invention provides methods of using enantiomers and enantiomeric mixtures of compounds represented by Formula I. A carbamate enantiomer of Formula I contains an asymmetric chiral carbon at the benzylic position, which is the second aliphatic carbon adjacent to the phenyl ring.

An enantiomer that is isolated is one that is substantially free of the corresponding enantiomer. Thus, an isolated enantiomer refers to a compound that is separated via separation techniques or prepared free of the corresponding enantiomer.

The term "substantially free," as used herein, means that the compound is made up of a significantly greater proportion of one enantiomer. In preferred embodiments, the compound includes at least about 90% by weight of a preferred enantiomer. In other embodiments of the invention, the compound includes at least about 99% by weight of a preferred enantiomer. Preferred enantiomers can be isolated from racemic mixtures by any method known to those skilled in the art, including high performance liquid chromatography (HPLC) and the formation and crystallization of chiral salts, or preferred enantiomers can be prepared by methods described herein.

Carbamate Compounds as Pharmaceuticals:

The present invention provides racemic mixtures, enantiomeric mixtures and isolated enantiomers of Formula I as pharmaceuticals. The carbamate compounds are formulated as pharmaceuticals to provide treatment for EDS and related conditions in a subject.

In general, the carbamate compounds of the present invention can be administered as pharmaceutical compositions by any method known in the art for administering therapeutic drugs including oral, buccal, topical, systemic (e.g., transdermal, intranasal, or by suppository), or parenteral (e.g., intramuscular, subcutaneous, or intravenous injection.) Administration of the compounds directly to the nervous system can include, for example, administration to intracerebral, intraventricular, intracerebealventricar, intrathecal, intracisternal, intraspinal or peri-spinal routes of administration by delivery via intracranial or intravertebral needles or catheters with or without pump devices.

Compositions can take the form of tablets, pills, capsules, semisolids, powders, sustained release formulations, solutions, suspensions, emulsions, syrups, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, can be found in such standard references as Alfonso AR: *Remington's Pharmaceutical Sciences,* 17th ed., Mack Publishing Company, Easton Pa., 1985, the disclosure of which is incorporated herein by reference in its entirety and for all purposes. Suitable liquid carriers, especially for injectable solutions, include water, aqueous saline solution, aqueous dextrose solution, and glycols.

The carbamate compounds can be provided as aqueous suspensions. Aqueous suspensions of the invention can contain a carbamate compound in admixture with excipients suitable for the manufacture of aqueous suspensions. Such excipients can include, for example, a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate).

The aqueous suspension can also contain one or more preservatives such as ethyl or n-propyl p-hydroxybenzoate, one or more coloring agents, one or more flavoring agents, and one or more sweetening agents, such as sucrose, aspartame or saccharin. Formulations can be adjusted for osmolarity.

Oil suspensions for use in the present methods can be formulated by suspending a carbamate compound in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these.

Suitable emulsifying agents include naturally occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compound of choice, alone or in combination with other suitable components can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations of the present invention suitable for parenteral administration, such as, for example, by intraarticular (in the joints), intravenous, intramuscular, intradermal, intraperitoneal, and subcutaneous routes, can include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono-or diglycerides. In addition, fatty acids such as oleic acid can likewise be used in the preparation of injectables. These solutions are sterile and generally free of undesirable matter.

Where the compounds are sufficiently soluble they can be dissolved directly in normal saline with or without the use of suitable organic solvents, such as propylene glycol or polyethylene glycol. Dispersions of the finely divided compounds can be made-up in aqueous starch or sodium carboxymethyl cellulose solution, or in suitable oil, such as arachis oil. These formulations can be sterilized by conventional, well-known sterilization techniques. The formulations can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like.

The concentration of a carbamate compound in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally acceptable diluents or solvent, such as a solution of 1,3-butanediol. The formulations of commends can be presented in unit-dose or multi-dose sealed containers, such as ampoules and vials. Injection solutions and suspensions can be prepared from sterile powders, granules, and tablets of the kind previously described.

A carbamate compound suitable for use in the practice of this invention can be and is preferably administered orally. The amount of a compound of the present invention in the composition can vary widely depending on the type of composition, size of a unit dosage, kind of excipients, and other factors well known to those of ordinary skill in the art. In general, the final composition can comprise, for example, from 0.000001 percent by weight (% w) to 50% w of the carbamate compound, preferably 0.00001% w to 25% w, with the remainder being the excipient or excipients.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient.

Formulations suitable for oral administration can consist of (a) liquid solutions, such as an effective amount of the pharmaceutical formulation suspended in a diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions.

Pharmaceutical preparations for oral use can be obtained through combination of the compounds of the present invention with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxymethyl cellulose, hydroxypropylmethyl-cellulose or sodium carboxymethylcellulose; and gums including arabic and tragacanth; as well as proteins such as gelatin and collagen.

If desired, disintegrating or solubilizing agents can be added, such as the cross-linked polyvinyl pyrrolidone, agar, alginic acid, or a salt thereof, such as sodium alginate. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compounds of the present invention can also be administered in the form of suppositories for rectal administration of the drug. These formulations can be prepared by mixing the drug with a suitable non-irritating excipient that is solid at ordinary temperatures but liquid at the rectal temperatures and will therefore melt in the rectum to release the drug. Such materials are cocoa butter and polyethylene glycols.

The compounds of the present invention can also be administered by intranasal, intraocular, intravaginal, and intrarectal routes including suppositories, insufflation, powders and aerosol formulations (for examples of steroid inhalants, see Rohatagi, J. Clin. Pharmacol. 35:1187-1193, 1995; Tjwa, Ann. Allergy Asthma Immunol. 75:107-111,1995).

The compounds of the present invention can be delivered transdermally, by a topical route, formulated as applicator sticks, solutions, suspensions, emulsions, gels, creams, ointments, pastes, jellies, paints, powders, and aerosols.

Encapsulating materials can also be employed with the compounds of the present invention and the term "composition" can include the active ingredient in combination with an encapsulating material as a formulation, with or without other carriers. For example, the compounds of the present invention can also be delivered as microspheres for slow release in the body. In one embodiment, microspheres can be administered via intradermal injection of drug (e.g., mifepristone)-containing microspheres, which slowly release subcutaneously (see Rao, J. Biomater Sci. Polym. Ed. 7:623-645, 1995; as biodegradable and injectable gel formulations (see, e.g., Gao, Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months. Cachets can also be used in the delivery of the compounds of the present invention.

In another embodiment, the compounds of the present invention can be delivered by the use of liposomes which fuse with the cellular membrane or are endocytosed, i.e., by employing ligands attached to the liposome that bind to surface membrane protein receptors of the cell resulting in endocytosis. The active drug can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

By using liposomes, particularly where the liposome surface carries ligands specific for target cells, or are otherwise preferentially directed to a specific organ, one can focus the delivery of the carbamate compound into target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

The pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation can be a lyophilized powder which can contain, for example, any or all of the following: 1 mM-50 mM histidine, 0.1%-2% sucrose, 2%-7% mannitol, at a pH range of 4.5 to 5.5, that is combined with buffer prior to use.

Pharmaceutically acceptable salts and esters refers to salts and esters that are pharmaceutically acceptable and have the desired pharmacological properties. Such salts include salts that may be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N methylglucamine, and the like. Pharmaceutically acceptable salts can also include acid addition salts formed from the reaction of amine moieties in the parent compound with inorganic acids (e.g. hydrochloric and hydrobromic acids) and organic acids (e.g. acetic acid, citric acid, maleic acid, and the alkane-and arene-sulfonic acids such as methanesulfonic acid and benzenesulfonic acid). Pharmaceutically acceptable esters include esters formed from carboxy, sulfonyloxy, and phosphonoxy groups present in the compounds. When there are two acidic groups present, a pharmaceutically acceptable salt or ester may be a mono-acid-mono-salt or ester or a di-salt or ester; and similarly where there are more than two acidic groups present, some or all of such groups can be salified or esterified.

Compounds named in this invention can be present in unsalified or unesterified form, or in salified and/or esterified form, and the naming of such compounds is intended to include both the original (unsalified and unesterified) compound and its pharmaceutically acceptable salts and esters. The present invention includes pharmaceutically acceptable salt and ester forms of Formula (I). More than one crystal form of an enantiomer of Formula I can exist and as such are also included in the present invention.

A pharmaceutical composition of the invention can optionally contain, in addition to a carbamate compound, at least one other therapeutic agent useful in the treatment of EDS. For example the carbamate compounds of Formula I can be combined physically with other activating or stimulant compounds in fixed dose combinations to simplify their administration.

Methods of formulating pharmaceutical compositions have been described in numerous publications such as *Pharmaceutical Dosage Forms: Tablets*. Second Edition. Revised and Expanded. Volumes 1-3, edited by Lieberman et al; *Pharmaceutical Dosage Forms*: Parenteral Medications. Volumes 1-2, edited by Avis et al; and *Pharmaceutical Dosage Forms: Disperse Systems*. Volumes 1-2, edited by Lieberman et al; published by Marcel Dekker, Inc, the disclosure of which are herein incorporated by reference in their entireties and for all purposes.

The pharmaceutical compositions are generally formulated as sterile, substantially isotonic and in full compliance with all Good Manufacturing Practice (GMP) regulations of the U.S. Food and Drug Administration.

Dosage Regimens

The present invention provides methods of providing treatment for EDS and related conditions in a mammal using carbamate compounds. The amount of the carbamate compound necessary to provide treatment for EDS and related conditions is defined as a therapeutically or a pharmaceutically effective dose. The dosage schedule and amounts effective for this use, i.e., the dosing or dosage regimen will depend on a variety of factors including the stage of the disease, the patient's physical status, age and the like. In calculating the dosage regimen for a patient, the mode of administration is also taken into account.

A person of ordinary skill in the art will be able without undue experimentation, having regard to that skill and this disclosure, to determine a therapeutically effective amount of a particular substituted carbamate compound for practice of this invention (see, e.g., Lieberman, Pharmaceutical Dosage Forms (Vols. 1-3, 1992); Lloyd, 1999, The art, Science and Technology of Pharmaceutical Compounding; and Pickar, 1999, Dosage Calculations). A therapeutically effective dose is also one in which any toxic or detrimental side effects of the active agent is outweighed in clinical terms by therapeutically beneficial effects. It is to be further noted that for each particular subject, specific dosage regimens should be evaluated and adjusted over time according to the individual need and professional judgment of the person administering or supervising the administration of the compounds.

For treatment purposes, the compositions or compounds disclosed herein can be administered to the subject in a single bolus delivery, via continuous delivery over an extended time period, or in a repeated administration protocol (e.g., by an hourly, daily or weekly, repeated administration protocol). The pharmaceutical formulations of the present invention can be administered, for example, one or more times daily, 3 times per week, or weekly. In one embodiment of the present invention, the pharmaceutical formulations of the present invention are orally administered once or twice daily.

In this context, a therapeutically effective dosage of the biologically active agent(s) can include repeated doses within a prolonged treatment regimen that will yield clinically significant results to provide treatment for EDS and related conditions. Determination of effective dosages in this context is typically based on animal model studies followed up by human clinical trials and is guided by determining effective dosages and administration protocols that significantly reduce the occurrence or severity of targeted exposure symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and histopathologic assays).

Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response).

In an exemplary embodiment of the present invention, unit dosage forms of the compounds are prepared for standard administration regimens. In this way, the composition can be subdivided readily into smaller doses at the physician's direction. For example, unit dosages can be made up in packeted powders, vials or ampoules and preferably in capsule or tablet form.

The active compound present in these unit dosage forms of the composition can be present in an amount of, for example, from about 10 mg to about one gram or more, for single or multiple daily administration, according to the particular need of the patient. By initiating the treatment regimen with a minimal daily dose of about one gram, the blood levels of the carbamate compounds can be used to determine whether a larger or smaller dose is indicated.

Effective administration of the carbamate compounds of this invention can be administered, for example, at an oral or parenteral dose of from about 0.01 mg/kg/dose to about 150 mg/kg/dose. Preferably, administration will be from about 0.1/mg/kg/dose to about 25 mg/kg/dose, more preferably from about 0.2 to about 18 mg/kg/dose. Therefore, the therapeutically effective amount of the active ingredient contained per dosage unit as described herein can be, for example, from about 1 mg/day to about 7000 mg/day for a subject having, for example, an average weight of 70 kg.

The methods of this invention also provide for kits for use in providing treatment for EDS and related conditions. After a pharmaceutical composition comprising one or more carbamate compounds of this invention, with the possible addition of one or more other compounds of therapeutic benefit, has been formulated in a suitable carrier, it can be placed in an appropriate container and labeled for providing treatment for EDS and related conditions. Additionally, another pharmaceutical comprising at least one other therapeutic agent can be placed in the container as well and labeled for treatment of the indicated disease. Such labeling can include, for example, instructions concerning the amount, frequency and method of administration of each pharmaceutical.

Although the foregoing invention has been described in detail by way of example for purposes of clarity of understanding, it will be apparent to the artisan that certain changes and modifications are comprehended by the disclosure and may be practiced without undue experimentation within the scope of the appended claims, which are presented by way of illustration not limitation. The following examples are provided to illustrate specific aspects of the invention and are not meant to be limitations.

EXAMPLE

Study Purpose:

This study was undertaken to determine the effect of the (D) or (R) enantiomer of a phenylalkylamino carbamate of Formula I, specifically O-carbamoyl-(D)-phenylalaninol which can also be named (R)-(beta-amino-benzenepropyl) carbamate shown above as Formula Ib, referred to herein as "TEST COMPOUND" on the sleep-wake organization in rats after acute administration of test compound, in direct comparison to amphetamine and cocaine.

In order to characterize the profile of activity of TEST COMPOUND in sleep-wake organization in rats, animals were chronically implanted with electrodes for recording the cortical electroencephalogram, electrical neck muscle activity, and ocular movements, while whole body movement levels were simultaneously registered. Secondly, effects were compared with those obtained with two reference psychostimulant drugs, cocaine and amphetamine. Changes in sleep-wake organization can be reliably detected on the basis of such polysomnographic recordings. Subsequent analysis of the pattern of changes has been validated to predict the class of psychotropic agents to which the compound under investigation resembles best. (See, Ruigt, G S et al. (1993) *Neuropsychobiology,* 28(3):138-153)

Materials and Methods

Animals

The experiments were carried out on male adult Sprague Dawley rats, supplied by Harlan (Borchen, Germany) weighing 240-260 g at time of surgery. Animals were housed in full-view Plexiglas cages (25×33×18 cm) that fit to IVC-racks (individually ventilated cages) located in a sound attenuated chamber. Rats were provided with a micro-chip for identification purposes and maintained under controlled environmental conditions throughout the study: 22±2° C. ambient temperature, relative humidity at 60%, 12:12 light-dark cycle (lights on from 12:00 hrs to 00:00 hrs; light intensity~100 lux) with standard laboratory food chow and tap water available ad libitum. The institutional animal care and use committee approved all animal procedures.

Surgery

Under isoflurane inhalation anesthesia, the rats were mounted in a stereotaxic apparatus. The oval area of the scalp was removed, and the uncovered skull was cleared of the periosteum. Three small cavities were drilled into the cranial bone without perforating the dura to receive 3 fixing stainless steel screws (diameter 1 mm) for polygraphic recording of frontal and parietal electroencephalogram (EEG). Two electrodes were placed stereotaxically on each side of the sagittal suture (AP+2 mm, L−2 mm; and AP−6 mm, L 3 mm from Bregma, while the third (reference) electrode was screwed over the cerebellum. The incisor bar was −5 mm under the centre of the ear bar, according to the stereotactic atlas of Paxinos G. & Watson C. *The Rat Brain in Stereotaxic Coordinates*, Academic Press, San Diego, Calif., U.S.A. (1998).

For the recording of the electro-oculogram (EOG) and electromyogram (EMG), stainless steel wires were placed in peri-orbital, and inserted into nuckal muscle, respectively. Electrodes (stainless steel wire, 7N51465T5TLT, 51/46 Teflon Bilaney, Germany) were connected to a pin (Future Electronics: 0672-2-15-15-30-27-10-0) with a small insert (track pins; Dataflex: TRP-1558-0000) were fitted into a 8 holes connector. Finally, the electrodes were fixed with dental cement to the cranium. The animals were housed individually and were allowed to recover for at least one week.

Sleep Recording Procedure and Pharmacological Test

Ten days after surgery, the animals were habituated for two weeks to the recording procedure in their home cages. The rats were connected at regular intervals with a cable to a rotating swivel allowing free movements while EEG, EOG and EMG activities were monitored.

Only rats that complied with the required criteria were used at time of testing i.e. weight of animals 300-700 g, good polygraphical signal quality, a wash out period of at least 14 days in case of subject reuse, and no failure in two successive test sessions. For each compound, two EEG recording sessions were performed in 32 operated animals that were randomly assigned to 4 treatment conditions (n=8 rats per condition).

The first recording session started at 14:00 hrs and lasted 16 hours after administration of saline (n=32 rats). The second recording session was performed for the same duration following administration of saline and different doses of TEST COMPOUND (1, 3 and 10 mg/kg), cocaine (3, 10 and 30 mg/kg i.p.), or amphetamine (3, 10, 30 mg/kg i.p.). All compounds were dissolved in saline and administered in a volume of 10-ml/kg-body weight. An equivalent volume of saline was administered in control conditions. The EEG, EOG, EMG signals and body movement activities were monitored for 16 hours. The acquisition of data was performed with a sample rate of 200 Hz. All signals were passed via a bipolar recorder system (Embla) developed by MedCare (Iceland) to a computer and managed by a software package (Somnologica, MedCare, Iceland) which turns the computer into a polygraphic workstation for signal recording.

Sleep-Wake Organization Analysis

The automated rat sleep analysis system was applied to 16 continuous hours following the injection of the compound. Off-line, the sleep-wake staging was in an automated fashion executed per 2-second epochs and averaged for 30-minutes periods, based on 5 EEG frequency domain values ($\delta$: 0.4-4 Hz, $\theta$: 4.2-8 Hz, $\alpha$: 8.2-12 Hz, $\sigma$: 12.2-14 Hz, $\beta$: 14.2-30 Hz), integrated EMG, EOG and body activity level.

The discriminative analysis uses classification rules for the final sleep stage assignment of each specific EEG epoch. The six sleep stages were classified as being indicative of either active wakefulness (AW), passive wakefulness (PW), light slow wave sleep (lSWS), deep slow wave sleep (dSWS), intermediate stage (IS) or rapid eye movement sleep (REMS). Briefly, the different vigilance states were characterized as follows: AW, low-voltage fast EEG activity, high EMG activity, numerous eye movements and high body activity; PW, low-voltage fast EEG activity, high to moderate EMG activity, numerous eye movements and absence of body activity; lSWS, high-voltage slow cortical waves interrupted by low-voltage fast waves and reduced EMG activity; dSWS, continuous high-amplitude slow-wave activity in EEG in absence of EMG, EOG and body activities; IS: transient spindle activity with theta rhythm, absence of EOG and body movements;

REMS: low-voltage fast cortical waves with a regular theta rhythm, presence of rapid eye movements and absence of muscular and body movements.

The scores were synchronized in time with the EEG signal and the system calculated automatically different sleep-wake parameters such as amount of time spent in each state, number and duration of episodes in each vigilance state, latencies for lSWS, dSWS and REMS and the number of shifts from one state to another one. For each sleep state, the latency was defined as the time between the beginning of the recording and the appearance of the first sleep period lasting at least 30 seconds.

Statistical Analysis

Time spent in each vigilance state (AW, PW, lSWS, dSWS, IS and REMS) were expressed in percentage of the recording period. A statistical analysis of the obtained data was carried out by a non parametric analysis of variance per 30-min periods followed by a Wilcoxon-Mann-Whitney rank sum tests in comparisons with the control group.

Effects of Test Compound

The administration of TEST COMPOUND produced significant changes in the distribution of sleep-wake states.

A slight modification of the sleep-wake architecture was observed throughout the 16 hours recording period following the administration of the lowest dose of the compound (3 mg/kg i.p.). An increase in total light sleep (+26%, $p<0.05$) and an increased drive to wakefulness from light sleep as well as deep sleep (+46%, $p<0.001$; +15%, $p<0.05$; respectively) were observed indicating aspects of sleep fragmentation following this dose of the compound ($p<0.05$) (see Table 4).

At the dose of 10 mg/kg i.p. TEST COMPOUND produced changes in the sleep wake organization associated with a significant increase in total duration of light sleep (+24%, $p<0.05$) and a significant increase in shifts from REM sleep towards active wakefulness. (+16%, $p<0.05$) (See Tables 2 and 4). During the first 90 minutes of the recording period a significant decrease in deep sleep duration in favor of increase in time spent in active wakefulness was observed, ($p<0.05$).

At the highest dose (30 mg/kg i.p.) test compound produced pronounced changes in the distribution of the sleep-wake cycle. A marked increase of the total time spent in the active wakefulness (+19%, $p<0.05$), a reduction of total time spent in passive wakefulness (−29%, $p<0.05$), in light sleep (−20%, $p<0.05$) as well as REM sleep (−25%, $p<0.05$) over the course of the 16-h post-injection period of the registration (see Table 2). In addition, when compared to total sleep time, TEST COMPOUND induced an increase in time spent in deep sleep and decreased time in REM sleep ($p<0.05$) (see Table 4).

A significant enhancement of active wakefulness was observed during the first 3 hours following the administration of TEST COMPOUND ($p<0.01$). Concomitantly, a large reduction in the time spent in sleep e.g. light sleep ($p<0.01$), deep sleep ($p<0.01$) and REM sleep ($p<0.01$), followed by a rebound effect particularly an increase in deep sleep after 3 hours following the administration of TEST COMPOUND. The latter effect lasted about 7 hours during the light period of the recording. It should be noted that the onset of activity of TEST COMPOUND was almost immediate namely around the first 30 minutes following administration.

The large increase in total time spent in active wakefulness and the reduction in passive wakefulness, light sleep and REM sleep were due to an increase (+19%, $p<0.05$), and a decrease (−30%, $p<0.05$; −23%, $p<0.05$; −24%, $p<0.01$) in the number of epochs of these sleep-wake stages, respectively. However, the mean durations of these sleep wake states were not modified. As depicted (see Table 4) TEST COMPOUND at 30 mg/kg produced an increase in the number of shifts from light sleep and REM sleep towards wakefulness ($p<0.05$) and thus suggests indications of sleep fragmentation. Examination of sleep latencies revealed significant changes following TEST COMPOUND administration (see Table 1). TEST COMPOUND at 10 and 30 mg/kg produced a significant lengthening of the latencies of REM sleep onset.

Effects of Cocaine

The major modifications in sleep architecture following the administration of cocaine were observed with the highest dose tested i.e. a decrease in total time spent in REM sleep (−18%) sleep namely in favour of an increase in total duration of active wakefulness (+14%) throughout 16 hours recording following the treatment. Additionally, no effects of cocaine at the different doses tested were observed on total sleep time as well as on the number of shifts from sleep toward wakefulness.

Cocaine at the dose of 10 mg/kg produced a significant increase in the duration of active wakefulness over a three hours period following the treatment (0.5 h: +111%, $p<0.001$; 1 h: +500%, $p<0.001$; 1.5 hr: +312%, $p<0.001$; 2 h: +120%, $p<0.001$; 2.5 hr: +166%, $p<0.001$; 3 hr: +77%, $p<0.001$). Concomitantly, the time spent in light sleep as well as in deep sleep was decreased during the initial 2 hours of the recording time (0.5 h: −100% and 90%, $p<0.001$; 1 h: −99% and −100%, $p<0.001$; 1.5 hr: −87% and −99%, $p<0.001$; 2 h: −25% and −70%, $p<0.05$ and $p<0.001$; respectively). Additionally, the duration of REM sleep was significantly decreased during the first 3 hours period after administration (0.5 hr, 1 hr, 1.5 hr: each −100%, $p<0.001$; 2 hr: −87%, $p<0.001$; −2.5 hr: −47%, $p<0.001$, 3 hr: −78%, $p<0.001$).

The increased amount of active wakefulness following the administration of cocaine at the dose of 10 mg/kg resulted from an increase in the number of epochs (0.5 h: +111%, $p<0.001$; 1 h: +500%, $p<0.001$; 1.5 hr: +312%, $p<0.001$; 2 h: +119%, $p<0.001$; 2.5 hr: +166%, $p<0.05$; 3 hr: +77%, $p<0.001$) while the mean duration of this state was not affected.

The reduction of time spent in light sleep and deep sleep during the first 2 hours of the recording period was due to a decrease in number of epochs of these states (0.5 h: −100% and −100%, $p<0.001$; 1 hr: −99% and −100%, $p<0.001$; 1.5 h: −87% and −100%, $p<0.001$; 2 hr: −22% and −38%, $p<0.05$, respectively). Likewise, the decrease in time duration spent in REM sleep during the first 3 hours derived from a reduction in number of epochs of this state (0.5 hr, 1 hr, 1.5 hr: each −100%, $p<0.001$; 2 hr: −87%, $p<0.001$; −2.5 hr: −47%, $p<0.00$; 3 hr: −78%, $p<0.001$), respectively.

As shown in Table 1, REM sleep onset latencies were dose dependently affected ($p<0.05$).

Effects of Amphetamine

During the total recording period of 16 hours, amphetamine at 1, 3, and 10 mg/kg produced significant changes in sleep-wake organization. Amphetamine dose-dependently increased the total time spent in active wakefulness (+27%, $p<0.05$; +47%, $p<0.001$; +66%, $p<0.001$), deep (rebound) sleep (+73%, $p<0.05$; +91%, $p<0.05$; +66%, $p<0.001$), and decreased the total time spent in light sleep (−35%, $p<0.05$; −49%, $p<0.05$; −51%, $p<0.001$), and REM sleep (−4%; −22%, $p<0.05$; −41%, $p<0.001$), respectively (See Table 2). Moreover, when compared to vehicle, amphetamine at 3 and 10 mg/kg proportionally reduced total sleep time ($p<0.001$) and time spent in light sleep, while the compound increased the proportion of deep sleep compared to total time spent asleep ($p<0.05$) (see Table 3). The large increase in active wakefulness and deep sleep following the administration of 1, 3, and 10 mg/kg of amphetamine resulted from an increase in the number of active wake epochs (+27%, $p<0.05$; +47%, $p<0.001$; +66%, $p<0.001$; respectively) and deep sleep epochs (+73%, $p<0.001$; +91%, $p<0.001$; +66%, $p<0.001$). While the mean duration of active wake was not modified for different doses of the compound, the mean duration of deep sleep stage was reduced following 3 and 10 mg/kg of the compound (−19%, $p<0.05$; −30%, $p<0.05$).

The reduction in light SWS and REM sleep total time after the administration of 1, 3, and 10 mg/kg of amphetamine were due to a decrease in the number of light sleep epochs (−35%, $p<0.05$; −49%, $p<0.001$; −51%, $p<0.001$; respectively), and REM sleep epochs (−4%; −22%, $p<0.05$; −41%, $p<0.001$; respectively. The mean duration of REM sleep stage were decreased (−16%, $p<0.05$; −23%, $p<0.05$; −36%, $p<0.05$; respectively), while this parameter was not significantly modified for light sleep. Amphetamine enhanced active wakefulness in a clearly dose-dependent fashion during a period of 3, 4, and 6 hours (1, 3, and 10 mg/kg respectively; $p<0.05$;). Concomitantly, a dose dependent reduction in light, deep and REM sleep durations as observed over a period of 3, 4, 6 hours ($p<0.05$, respectively) following administration.

Amphetamine had a biphasic effect on the time spent in deep sleep stage i.e. it was largely reduced during 3-6 hours following the injection and then increased as a likely rebound effect during the light period of the recording.

As indicated in Table 1, amphetamine significantly affected sleep parameters by lengthening the onset latencies of sleep states ($p<0.001$).

Results:

Minor changes in vigilance states were observed after the administration of TEST COMPOUND at the dose of 3 and 10 mg/kg. However, treatment with TEST COMPOUND at 30 mg/kg strongly increased active wakefulness at the expense of time spent in light sleep, deep sleep and REM sleep during the first 3 to 4 hours after the administration. A rebound effect was seen between 4-10 hours following administration of the compound, as an increase in time spent in deep sleep that gradually decreased in the hours thereafter. Moreover, TEST COMPOUND affected other sleep-wake parameters; more specifically it increased significantly the number of shifts from light sleep and REM sleep into wakefulness as well as lengthened the latency of REM sleep onset.

Cocaine administered at the dose of 1 and 3 mg/kg only slightly affected the sleep-wake organization. In contrast, cocaine at 10 mg/kg significantly enhanced active wakefulness and reduced slow wave sleep and REM sleep during the first 3 to 4 hours following injection of the compound. All sleep latencies were increased. Amphetamine dose-dependently increased wakefulness and reduced all sleep states during 3 to 8 hours following administration. A clear dose-dependent rebound effect was observed for deep. Additionally, the latencies of all sleep states were significantly increased.

CONCLUSIONS

The present findings show that almost immediately after intraperitoneal injection TEST COMPOUND was centrally active for at least 4 hours with a peak in effect around 2 hours post administration. Only minor effects on sleep-wake architecture were observed at the lowest dose tested of 3 mg/kg. Changes in the sleep parameters were observed with the middle (10 mg/kg) and more specifically with the higher dose of 30 mg/kg tested. The modifications of the sleep-wake distribution which were most obvious during the first 3 hours of the registration period were characterized by an large increase of time spent in active wakefulness, while time spent in passive wakefulness, light sleep, deep sleep and REM sleep was reduced. Interestingly, TEST COMPOUND produced a rebound effect of recovery deep sleep associated with a marked increase in time spent in this state up to 7 hours.

The effects observed in this comparative study clearly suggest that TEST COMPOUND at 30 mg/kg has psychostimulant-like proprieties at the beginning of the administration while a consequently following increase in sleep propensity as shown by deep sleep enhancement point towards a potential indirect effect on sleep homeostasis.

The overall TEST COMPOUND profile of effects at 30 mg/kg was remarkably similar to the profile observed following the administration of amphetamine at the lowest dose tested of 1 mg/kg, both in terms of effect pattern, size and duration.

Therefore, TEST COMPOUND showed, in rats, central activity immediately after injection as expressed in changes sleep-wake architecture with a functional peak in effect around 2 hrs after i.p. administration. The findings show that TEST COMPOUND produced a biphasic effect i.e. an initial increase in wakefulness and reduction in sleep was followed by an increase in (deep) sleep, most likely a rebound effect, which lasted for 4-10 hours. These findings resemble closely the effects on sleep-wake architecture observed following administration of psychostimulant drugs; most specifically amphetamine at the lowest dose tested (i.e. at 1 mg/kg i.p.). Consequently, outcomes suggest that TEST COMPOUND is likely to have stimulant-like proprieties immediately after administration.

TABLE 1

Effects of R228060 (3, 10, 30 mg/kg i.p.), cocaine (1, 3, 10 mg/kg i.p.) and amphetamine (1, 3, 10 mg/kg i.p.) on the onset lafencies of different sleep states during 16 hours recording period following the administration.

| | | Latency (min) | | |
|---|---|---|---|---|
| | | ISWS | dSWS | REM sleep |
| Vehicle (i.p.) | | 14.2 ± 2.1 | 38.2 ± 15.0 | 50.5 ± 8.5 |
| R228060 (mg/kg i.p.) | 3 | 15.6 ± 4.1 | 42.0 ± 8.5 | 66.0 ± 11.8 |

TABLE 1-continued

Effects of R228060 (3, 10, 30 mg/kg i.p.), cocaine (1, 3, 10 mg/kg i.p.) and amphetamine (1, 3, 10 mg/kg i.p.) on the onset lafencies of different sleep states during 16 hours recording period following the administration.

| | | Latency (min) | | |
|---|---|---|---|---|
| | | ISWS | dSWS | REM sleep |
| R228060 (mg/kg i.p.) | 10 | 30.4 ± 7.9 | 127.2 ± 67.1 | 87.5 ± 14.5* |
| R228060 (mg/kg i.p.) | 30 | 73.6 ± 25.7 | 174.6 ± 12.3* | 251.8 ± 32.0* |
| Vehicle (i.p.) | | 18.6 ± 5.8 | 27.3.5 ± 8.4 | 39.0 ± 5.6 |
| Cocaine (mg/kg i.p.) | 1 | 69.9 ± 51.2 | 79.3 ± 26.7 | 74.3 ± 12.1* |
| Cocaine (mg/kg i.p.) | 3 | 41.5 ± 9.2* | 68.6 ± 7.6* | 112.0 ± 12.2* |
| Cocaine (mg/kg i.p.) | 10 | 101.8 ± 6.9* | 138.8 ± 8.7* | 192.1 ± 18.5* |
| Vehicle (i.p.) | | 16.1 ± 3.5 | 62.3 ± 11.5 | 93.4 ± 37.0 |
| Amphetamine (mg/kg i.p.) | 1 | 140.6 ± 13.4* | 161.7 ± 5.3* | 208.6 ± 14.4* |
| Amphetamine (mg/kg i.p.) | 3 | 228.2 ± 25.0 | 242.0 ± 19.4* | 338.6 ± 24.3* |
| Amphetamine (mg/kg i.p.) | 10 | 284.7 ± 56.1* | 367.3 ± 5.5* | 440.8 ± 57.8* |

Values are means ± s.e.m of 8 rats.

*$p < 0.05$: Wilcoxon-Mann-Whitney rank sum tests indicate statistical significance between drug and vehicle.

TABLE 2

Effects of R228060 (3, 10, 30 mg/kg i.p.), cocaine (1, 3, 10 mg/kg i.p.) and amphetamine (1, 3, 10 mg/kg i.p.) on the duration of different sleep states during 16 hours recording period following the administration.

| | | Duration (min) | | | | | |
|---|---|---|---|---|---|---|---|
| | | Active wake | Passive wake | Inter mediate stage | Light sleep | Deep sleep | REM sleep |
| Vehicle (i.p.) | | 313.0 ± 17.2 | 80.5 ± 8.0 | 5.1 ± 1.0 | 295.7 ± 21.5 | 152.7 ± 24.3 | 96.4 ± 4.5 |
| R228060 (mg/kg i.p.) | 3 | 290.0 ± 11.2 | 79.5 ± 10.7 | 2.9 ± 0.7* | 374.7 ± 16.6* | 125.0 ± 24.6 | 84.0 ± 5.4 |
| R228060 (mg/kg i.p.) | 10 | 305.5 ± 15.1 | 73.4 ± 13.2 | 5.2 ± 0.7 | 366.6 ± 21.2* | 104.0 ± 19.3 | 102.3 ± 4.6 |
| R228060 (mg/kg i.p.) | 30 | 371.6 ± 7.7* | 57.3 ± 4.7* | 4.0 ± 1.0 | 235.8 ± 14.3* | 214.9 ± 15.6 | 72.9 ± 7.3* |
| Vehicle (i.p.) | | 304.3 ± 27.5 | 54.1 ± 11.5 | 5.9 ± 1.0 | 317.1 ± 26.3 | 181.4 ± 20.1 | 91.2 ± 5.1 |
| Cocaine (mg/kg i.p.) | 1 | 331.5 ± 41.5 | 69.8 ± 11.0 | 6.7 ± 1.0 | 293.2 ± 26.3 | 162.9 ± 26.3 | 84.2 ± 8.1 |
| Cocaine (mg/kg i.p.) | 3 | 324.8 ± 18.3 | 66.7 ± 8.9 | 5.7 ± 0.6 | 303.2 ± 42.5 | 172.6 ± 34.3 | 76.7 ± 6.3 |
| Cocaine (mg/kg i.p.) | 10 | 347.3 ± 16.5 | 55.0 ± 10.4 | 6.3 ± 1.1 | 294.6 ± 24.4 | 171.9 ± 23.8 | 74.7 ± 7.5 |
| Vehicle (i.p.) | | 301.0 ± 18.7 | 74.4 ± 12.0 | 5.7 ± 1.0 | 371.7 ± 20.6 | 108.9 ± 23.7 | 91.5 ± 7.8 |
| Amphetamine (mg/kg i.p.) | 1 | 382.4 ± 19.6* | 50.0 ± 19.6* | 4.0 ± 19.6* | 242.7 ± 19.6* | 188.0 ± 19.6* | 88.6 ± 19.6 |
| Amphetamine (mg/kg i.p.) | 3 | 441.8 ± 15.7* | 43.5 ± 4.4* | 4.0 ± 1.0* | 187.9 ± 23.9* | 207.6 ± 17.7* | 71.4 ± 4.1* |
| Amphetamine (mg/kg i.p.) | 10 | 498.7 ± 19.0* | 35.6 ± 4.7* | 4.0 ± 1.0* | 182.0 ± 26.3* | 181.2 ± 22.0* | 53.6 ± 5.0* |

Values are means ± s.e.m of 8 rats.

*$p < 0.05$: Wilcoxon-Mann-Whitney rank sum tests indicate statistical significance of the vehicle-drug comparisons

TABLE 3

Effects of R228060 (3, 10, 30 mg/kg i.p.), cocaine (1, 3, 10 mg/kg i.p.), amphetamine (1, 3, 10 mg/kg i.p.) and the vehicle on sleep parameters during 16 hours recording period following the administration.

| | | Total sleep time (min) | | | |
|---|---|---|---|---|---|
| | | TST (min) | lSWS/TST (%) | dSWS/TST (%) | REMS/TST (%) |
| Vehicle (i.p.) | | 550.0 ± 15.7 | 53.7 ± 3.7 | 27.7 ± 4.2 | 17.6 ± 1.0 |
| R228060 (mg/kg i.p.) | 3 | 586.6 ± 20.0 | 64.3 ± 3.3 | 20.8 ± 3.8 | 14.4 ± 1.0 |
| R228060 (mg/kg i.p.) | 10 | 578.1 ± 22.6 | 63.5 ± 2.7 | 17.7 ± 3.1 | 17.8 ± 1.0 |
| R228060 (mg/kg i.p.) | 30 | 527.0 ± 7.9 | 44.9 ± 2.9 | 39.2 ± 2.9* | 13.7 ± 1.3* |
| Vehicle (i.p.) | | 595.6 ± 30.6 | 53.1 ± 3.3 | 30.3 ± 2.7 | 15.6 ± 1.1 |
| Cocaine (mg/kg i.p.) | 1 | 547.0 ± 51.5 | 51.8 ± 4.5 | 31.2 ± 4.8 | 15.4 ± 0.9 |
| Cocaine (mg/kg i.p.) | 3 | 558.2 ± 21.2 | 53.8 ± 6.3 | 31.4 ± 6.1 | 13.8 ± 1.1 |
| Cocaine (mg/kg i.p.) | 10 | 547.6 ± 18.2 | 53.8 ± 4.0 | 31.3 ± 4.2 | 13.8 ± 1.5 |
| Vehicle (i.p.) | | 577.9 ± 24.9 | 64.6 ± 3.1 | 18.5 ± 2.7 | 16.0 ± 1.3 |
| Amphetamine (mg/kg i.p.) | 1 | 523.3 ± 25.3 | 45.1 ± 5.3* | 36.6 ± 5.7* | 16.9 ± 0.9 |
| Amphetamine (mg/kg i.p.) | 3 | 460.9 ± 12.0* | 38.3 ± 3.4* | 46.0 ± 3.0* | 14.7 ± 0.7 |
| Amphetamine (mg/kg i.p.) | 10 | 422.9 ± 19.5* | 43.2 ± 5.7* | 42.9 ± 5.3* | 13.0 ± 0.9 |

Values are means ± s.e.m of 8 rats.
*$p < 0.05$: Wilcoxon-Mann-Whitney rank sum tests indicate statistical significance of the vehicle-drug comparisons.

TABLE 4

Effects of R228060 (3, 10, 30 mg/kg i.p.), cocaine (1, 3, 10 mg/kg i.p.), amphetamine (1, 3, 10 mg/kg i.p.) and the vehicle on the number of shifts from different sleep states towards wakefulness during 16 hours recording period following the administration.

| | | Shifts (number) | | | | | |
|---|---|---|---|---|---|---|---|
| | | Shift from lSWS to | | Shift from dSWS to | | Shift from REMS to | |
| | | AW | PW | AW | PW | AW | PW |
| Vehicle (i.p.) | | 148.6 ± 33.1 | 115.1 ± 45.0 | 9.1 ± 6.2 | 39.1 ± 24.1 | 81.7 ± 23.1 | 8.1 ± 5.4 |
| R228060 (mg/kg i.p.) | 3 | 217.8 ± 55.5* | 78.1 ± 35.8 | 9.7 ± 6.6* | 6.6 ± 5.9* | 78.0 ± 21.6* | 3.7 ± 3.0 |
| R228060 (mg/kg i.p.) | 10 | 204.5 ± 56.4 | 84.4 ± 40.5 | 4.2 ± 3.1 | 12.5 ± 8.5 | 94.1 ± 24.0* | 8.9 ± 6.7 |
| R228060 (mg/kg i.p.) | 30 | 221.9 ± 58.3* | 74.2 ± 29.0* | 8.7 ± 5.3 | 17.6 ± 12.0 | 65.1 ± 21.8* | 4.1 ± 3.2* |
| Vehicle (i.p.) | | 228.1 ± 56.3 | 114.5 ± 48.3 | 10.6 ± 6.5 | 45.2 ± 28.1 | 77.5 ± 21.9 | 13.2 ± 7.7 |
| Cocaine (mg/kg i.p.) | 1 | 184.1 ± 48.1 | 128.6 ± 45.2 | 10.1 ± 5.6 | 66.6 ± 48.2 | 74.5 ± 21.5 | 17.0 ± 8.8 |
| Cocaine (mg/kg i.p.) | 3 | 218.5 ± 50.6 | 142.2 ± 48.5 | 10.2 ± 6.7 | 64.5 ± 42.6 | 56.0 ± 16.4 | 10.7 ± 6.9 |
| Cocaine (mg/kg i.p.) | 10 | 201.2 ± 53.6 | 132.6 ± 48.2 | 10.4 ± 6.2 | 37.6 ± 23.8 | 52.3 ± 16.5 | 9.2 ± 5.8 |
| Vehicle (i.p.) | | 204.0 ± 45.7 | 79.6 ± 40.1 | 9.1 ± 5.5 | 10.2 ± 8.9 | 74.2 ± 20.6 | 6.1 ± 4.3 |
| Amphetamine (mg/kg i.p.) | 1 | 198.8 ± 50.1 | 64.4 ± 30.5 | 11.7 ± 7.2 | 37.7 ± 30.0 | 66.5 ± 19.1 | 5.8 ± 4.8 |
| Amphetamine (mg/kg i.p.) | 3 | 178.7 ± 46.6 | 62.4 ± 26.1 | 14.8 ± 7.8 | 26.6 ± 16.8 | 59.3 ± 17.8 | 3.3 ± 2.6 |
| Amphetamine (mg/kg i.p.) | 10 | 201.7 ± 66.1 | 49.0 ± 25.5 | 9.7 ± 5.9 | 11.6 ± 8.9 | 50.0 ± 16.2* | 2.2 ± 1.9* |

Values are means ± s.e.m of 8 rats.
*$p < 0.05$: Wilcoxon-Mann-Whitney rank sum tests indicate statistical significance of the vehicle-drug comparisons.

REFERENCES CITED

All references cited herein are incorporated herein by reference in their entirety and for all purposes to the same extent as if each individual publication or patent or patent application was specifically and individually indicated to be incorporated by reference in its entirety for all purposes.

The discussion of references herein is intended merely to summarize the assertions made by their authors and no admission is made that any reference constitutes prior art.

Applicants reserve the right to challenge the accuracy and pertinence of the cited references.

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatus within the scope of the invention, in addition to those enumerated herein will be apparent to those skilled in the art from the foregoing description and accompanying drawings. Such modifications and variations are intended to fall within the scope of the appended claims. The present invention is to be limited only by the terms of the appended claims, along with the full scope of equivalents to which such claims are entitled.

What is claimed is:

1. A method of treating Excessive Daytime Sleepiness (EDS) in a subject, comprising administration, to a subject in need of such treatment, of a therapeutically effective amount of a compound of the Formula (I):

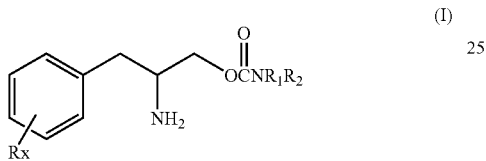

(I)

or a pharmaceutically acceptable salt thereof wherein R, $R_1$ and $R_2$ are hydrogen and x is 1.

2. A method of treating Excessive Daytime Sleepiness (EDS) in a subject, comprising the step of administration, to a subject in need of such treatment, of a therapeutically effective amount of an enantiomer of Formula I substantially free of other enantiomers or an enantiomeric mixture wherein one enantiomer of Formula I predominates;

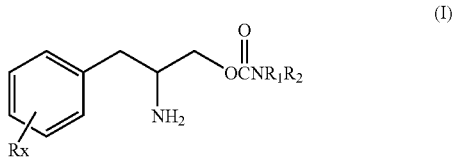

(I)

or a pharmaceutically acceptable salt thereof wherein R, $R_1$ and $R_2$ are hydrogen and x is 1.

3. The method of claim 2 wherein the enantiomer of Formula I predominates to the extent of about 90% or greater.

4. The method of claim 2 wherein the enantiomer of Formula I predominates to the extent of about 98% or greater.

5. The method of claim 2 wherein the enantiomer of Formula I is an enantiomer selected from the group consisting of Formula Ia

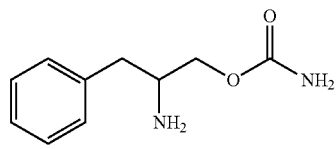 [SMILES: NC(=O)OCC(N)Cc1ccccc1]

or a pharmaceutically acceptable salt thereof.

6. The method of claim 5 wherein the enantiomer of Formula Ia is the (R) or (D) enantiomer.

7. The method of claim 5 wherein the enantiomer of Formula Ia is the (S) or (L) enantiomer.

8. The method of claim 5 wherein the enantiomer of Formula Ia predominates to the extent of about 90% or greater.

9. The method of claim 5 wherein the enantiomer of Formula Ia predominates to the extent of about 98% or greater.

10. The method of claim 2 wherein the enantiomer of Formula I substantially free of other enantiomers is the (D) or the (R) enantiomer of Formula Ib or an enantiomeric mixture wherein the (D) or (R) enantiomer of Formula Ib predominates

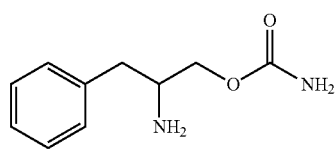 [SMILES: NC(=O)OCC(N)Cc1ccccc1]

Formula Ib (R)-(beta-amino-benzenepropyl) carbamate.

11. The method of claim 10 wherein the enantiomer of Formula Ib (R)-(beta-amino-benzenepropyl) carbamate predominates to the extent of about 90% or greater.

12. The method of claim 10 wherein the enantiomer of Formula Ib (R)-(beta-amino-benzenepropyl) carbamate predominates to the extent of about 98% or greater.

13. The method of claim 10 wherein the cause of the EDS is chosen from the group consisting of central nervous system (CNS) pathologic abnormalities, stroke, narcolepsy, idiopathic CNS hypersomnia; sleep deficiency, sleep apnea, obstructive sleep apnea, insufficient nocturnal sleep, chronic pain, acute pain, Parkinson's disease, urinary incontinence, multiple sclerosis fatigue, Attention Deficit Hyperactivity Disorder (ADHD), Alzheimer's disorder, Major Depression, Bipolar Disorder, cardiac ischemia; misalignments of the body's circadian pacemaker with the environment, jet lag, shift work; and sedating drugs.

14. The method of claim 10 wherein the cause of the EDS is narcolepsy.

15. The method of claim 10 wherein the therapeutically effective amount of (R)-(beta-amino-benzenepropyl) carbamate enantiomer is from about 0.01 mg/kg/dose to about 300 mg/kg/dose.

* * * * *

UNITED STATES PATENT AND TRADEMARK OFFICE
CERTIFICATE OF CORRECTION

PATENT NO. : 8,440,715 B2  
APPLICATION NO. : 11/921995  
DATED : May 14, 2013  
INVENTOR(S) : Ahnaou et al.

Page 1 of 1

It is certified that error appears in the above-identified patent and that said Letters Patent is hereby corrected as shown below:

On Title Page:

Item 75, Inventors: Please correct inventor
"Wilhelmus H.L.M. Drinkenburg, Molenschot (NL);"
to read -- Wilhelmus H.I.M. Drinkenburg, Molenschot (NL); --

In the Specification:

Column 1, Lines 6-7: Please correct "PCT/LJS2006/022407;"
to read -- PCT/US2006/022407; --

Column 8, Line 33: Please correct "Nos. 5,705,640, 5,955,499,"
to read -- Nos. 5,705,640, 5,756,817, 5,955,499, --

Signed and Sealed this
Twenty-fourth Day of December, 2013

Margaret A. Focarino
*Commissioner for Patents of the United States Patent and Trademark Office*